(12) United States Patent
Ranjan et al.

(10) Patent No.: US 8,565,373 B2
(45) Date of Patent: Oct. 22, 2013

(54) METHOD AND SYSTEM FOR AUTOMATICALLY POSITIONING A MAMMOGRAPHY IMAGING SYSTEM

(75) Inventors: Rajeev Ranjan, Bihar (IN); Raja Shekhara, Karnataka (IN)

(73) Assignee: General Electric Company, Schenectady, NY (US)

( * ) Notice: Subject to any disclaimer, the term of this patent is extended or adjusted under 35 U.S.C. 154(b) by 282 days.

(21) Appl. No.: 12/965,952

(22) Filed: Dec. 13, 2010

(65) Prior Publication Data

US 2011/0158383 A1 Jun. 30, 2011

(30) Foreign Application Priority Data

Dec. 29, 2009 (IN) .............. 3197/CHE/2009

(51) Int. Cl.
*A61B 6/04* (2006.01)
(52) U.S. Cl.
USPC ............... 378/37; 378/165; 378/205
(58) Field of Classification Search
USPC ........... 378/37, 162, 163, 165, 193, 195, 196, 378/205
See application file for complete search history.

(56) References Cited

U.S. PATENT DOCUMENTS

| 2003/0161439 A1 | 8/2003 | Eriksson et al. |
| 2007/0232881 A1 | 10/2007 | Shai et al. |
| 2007/0291897 A1 | 12/2007 | Ramsuer et al. |
| 2011/0004347 A1 | 1/2011 | Hornig |

FOREIGN PATENT DOCUMENTS

DE 102008011157 A1 9/2009

OTHER PUBLICATIONS

EP 10195038.4, European Search Report and Written Opinion, Mar. 23, 2011.

*Primary Examiner* — Jurie Yun
(74) *Attorney, Agent, or Firm* — Global Patent Operation; Marc A. Vivenzio

(57) ABSTRACT

A method and system for automatically adjusting the gantry position to the breast height level of a patient. The automated height adjustment system for mammography imaging systems having a movable gantry associated with a fixed vertical support, comprises a tracking unit for tracking a patient's breast height level during patient's initial mammography procedure; and memory for storing the tracked breast height level along with the patient identification information. The system further comprises a processor configured to access the breast height level using the patient identification information during subsequent mammography procedures for the patient; and a drive mechanism capable of automatically adjusting the height of the gantry based on the accessed breast height level.

16 Claims, 5 Drawing Sheets

METHOD AND SYSTEM FOR AUTOMATICALLY POSITIONING A MAMMOGRAPHY IMAGING SYSTEM

BACKGROUND OF THE INVENTION

1. Field of the invention

The field of the invention relates generally to mammography methods and systems, and more particularly to, a method and system for automatically adjusting the gantry position to the breast height level of a patient.

2. Description of Related Art

Mammography has earned a great deal of significance, as it is a method for detecting signs of breast cancer. To perform a mammography, a patient's breast needs to be aligned properly with the X-ray source and the image receptor. In today's scenario, every time a mammography patient undergoes X-ray examination, technicians performing the operation need to spend significant amount of time adjusting the gantry height to the patient's breast level. This manual process is cumbersome and is subject to error. Further, the positioning depends on the skill set of the technician positioning the patient for imaging. Even if the patient is appearing for a second mammography, the technician needs to adjust the gantry manually based on the patient's breast height level.

The current way of manually adjusting the gantry height not only consumes a major part of the technician's time but also reduces the efficiency of the imaging systems, in terms of optimal usage.

The patient needs to spend time for the procedure, and, in the case of an emergency, the time taken in proper positioning causes delay in the procedure.

Thus, there exists a need to provide a method and system for automatically adjusting the gantry position with respect to the breast level of a patient before a mammography procedure.

BRIEF DESCRIPTION OF THE INVENTION

The above-mentioned shortcomings, disadvantages and problems are addressed herein which will be understood by reading and understanding the following specification.

One embodiment of the present invention provides an automated height adjustment system for mammography imaging systems having a movable gantry associated with a fixed vertical support. The system comprises a tracking unit for tracking a patient's breast height level during patient's initial mammography procedure; memory for storing the tracked breast height level along with patient identification information; a processor configured to access the breast height level using the patient identification information, during subsequent mammography procedures of the patient; and a drive mechanism capable of automatically adjusting the height of the gantry based on the accessed breast height level.

In another embodiment, a mammography system is disclosed. The system comprises a fixed vertical member; a movable gantry, movable along the vertical member having an X-ray source and an image receptor; a tracking unit configured to track gantry position in a mammography procedure corresponding to a patient; memory configured to record the tracked gantry position; a drive mechanism configured to adjust the gantry position; and a processor associated with the drive mechanism, wherein the processor is configured to access the tracked gantry position corresponding to the patient and instruct the drive mechanism to adjust the gantry position based on the recorded gantry position.

In yet another embodiment, a method of automatically adjusting gantry position during a mammography procedure using a mammography imaging system is disclosed. The method comprises obtaining a patient's breast height level during patient's initial mammography procedure; recording the breast height level along with patient identification information; accessing the breast height level corresponding to a patient using the patient identification information during subsequent mammography procedures for the patient; and automatically adjusting height of the gantry based on the breast height level.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical, and other changes may be made without departing from the scope of the embodiments. The following detailed description is, therefore, not to be taken as limiting the scope of the invention.

Various embodiments of the present invention are directed to methods and systems for automatically adjusting gantry position with reference to the patient's breast height level. In an embodiment, the patient's breast height level is recorded during her initial mammography procedure and this information is used in positioning the gantry for subsequent examinations of the patient. In an embodiment, the patient's breast height level is provided through a user interface, based on which the gantry is positioned automatically. This will be helpful to automate the gantry positioning during the patient's initial mammography procedure or if the recorded information is not available.

Although the invention is explained with reference to patient breast height level and gantry position, the gantry position can be adjusted using other patient parameters as well. The other patient parameters could include patient demographic or physiological information. For example, average height of patients from a particular geography may be obtained and, based on the same, gantry level may be adjusted approximately. Similarly patient age, height, or weight could also be used in determining the gantry position.

Figure 1:
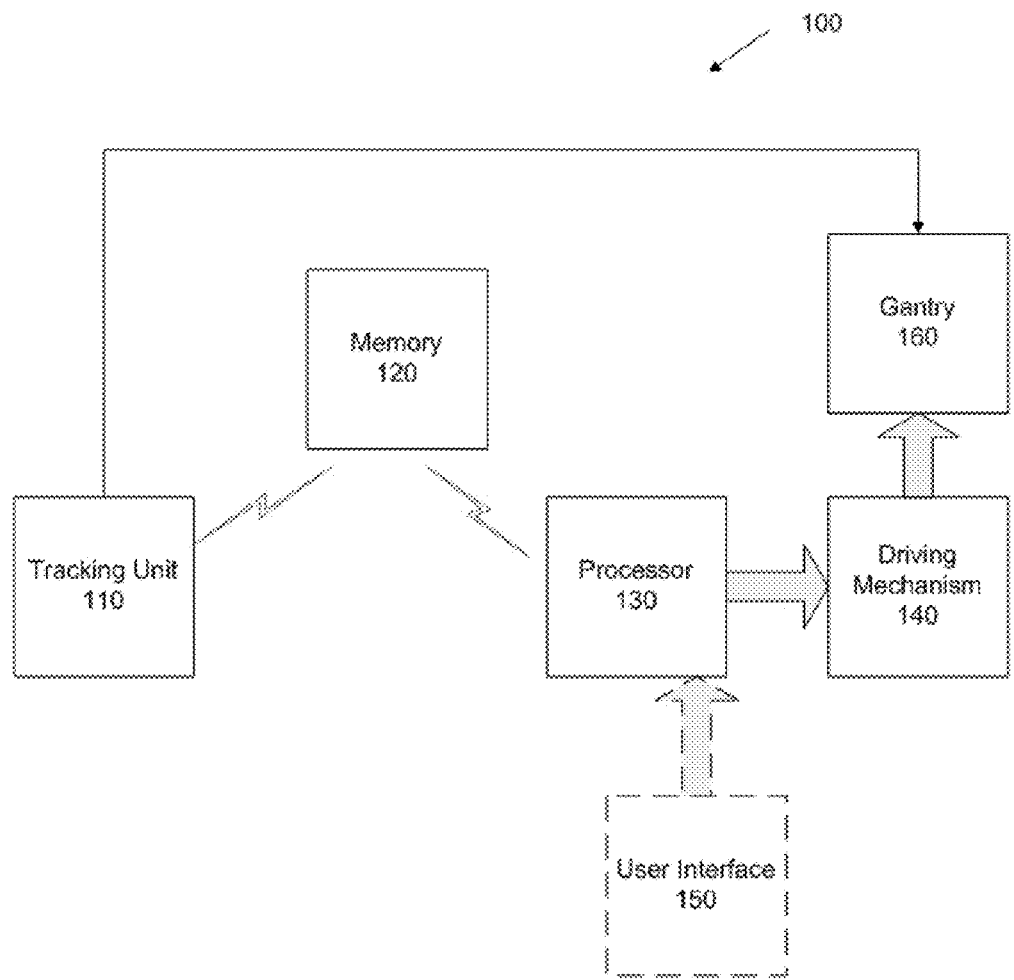
FIG. 1 is a block diagram of an automated height adjustment system for a mammography imaging system as described in an embodiment of the invention.

FIG. 1 is a block diagram of an automated height adjustment system for a mammography imaging system as described in an embodiment of the invention. The height adjustment system is used in association with the mammography system to automatically identify the patient breast height level and position the gantry based on the patient's breast level. The height adjustment system 100 comprises a tracking unit 110 configured to track the patient's breast height level and/or the gantry position and memory 120 to store the gantry position or the patient breast height level for a patient along with patient information. The system further comprises a processor 130 capable of accessing the gantry position or the patient breast height level from the memory 120. The processor 130 is further configured to instruct a drive mechanism 140 to automatically position the gantry 150 based on the accessed gantry position or breast height level information.

In an embodiment, the tracking unit 110 is configured to track the gantry position. The gantry position could be initially set by a clinician based on the patient's breast height level. Optionally, the system may be provided with a user interface 150 and through the user interface 150 a clinician/technician may input the desired gantry position. Based on the same, the drive mechanism 140 can position the gantry in accordance with the position information provided through the user interface 150. This could be done during the initial mammography procedure where the patient breast height level is not available. The gantry position information provided through the user interface 150 may be used, if the recorded patient breast height level information is not available.

In an embodiment, the technician may provide the patient breast height level through the user interface 150 and the user interface 150 in association with the processor 130 derive gantry position corresponding to the patient breast height level and the drive mechanism 140 may automatically adjust the gantry position based on the patient breast height level. The patient breast height level may be measured separately or using the tracking unit 110. Once the gantry level is adjusted, the gantry position or the patient's breast height level is recorded in the memory 120. The tracking unit 110 or any part of the unit or any device attached to the unit may communicate the breast height level or the gantry position to the memory and record the same.

During subsequent mammography procedure, the gantry position or the patient breast height level recorded can be accessed by the processor 130. The memory 120 is capable of receiving updates on the gantry position or the patient breast height level from the tracking unit 110. For each mammography procedure, the gantry position or the patient breast height level is obtained by the tracking unit 110 and if there is any change in the gantry position or the patient breast height level, the same is updated in the memory 120. The gantry position or the patient breast height level can be stored in an internal memory of the imaging system or in an external database such as Electronic Medical Record (EMR), Electronic Health Record (EHR), or any other database. Once the gantry position or the patient breast height level is recorded in the database, the gantry position or the patient breast height level can be accessed during subsequent mammography procedures. The gantry position or the patient breast height level is updated in the database upon noticing any changes from previously recorded height level.

The processor 130 may include dedicated hardware or software and/or firmware or a combination of dedicated hardware and software, or software in combination with a general purpose processor, or a digital signal processor. Once the requirements for such software, hardware, or dedicated hardware are gained from an understanding of the descriptions of embodiments of the invention contained herein, the choice of any particular implementation may be left to a hardware engineer or software engineer. The processor 130 is configured to access the gantry position or the patient breast height level from the internal memory or from the external database. The processor 130 may communicate through wireless or wired communication with the database. In an embodiment, the processor 130 is configured to derive the gantry position information if patient breast height level is provided.

Upon entering a patient for a mammography procedure, the processor 130 may obtain the patient identification information such as hospital number, name, age, etc. . . . The technician may input the patient identification information through the user interface 150. Alternately, the patient may be provided with some identification device and, using the same, the presence of the patient may be automatically determined by the processor 130. Once the patient identification information is obtained, the processor 130 fetches the recorded gantry position or patient breast height information corresponding to the patient and provides the recorded gantry position or patient breast height information to the drive mechanism 140. The drive mechanism 140, based on the gantry position information from the processor 140, adjusts the gantry position. Thus the gantry position will be adjusted with respect to the patient's breast height level automatically. The drive mechanism 140 could include any motor driven mechanism capable of moving the gantry.

In an embodiment, processor 130 may calculate approximate patient breast height level from patient's physiological information such as his height, age, etc. . . . This will assist a clinician in positioning the gantry automatically during the patient's initial mammography procedure or if the recorded gantry position or the patient breast height level is not available.

Figure 2:
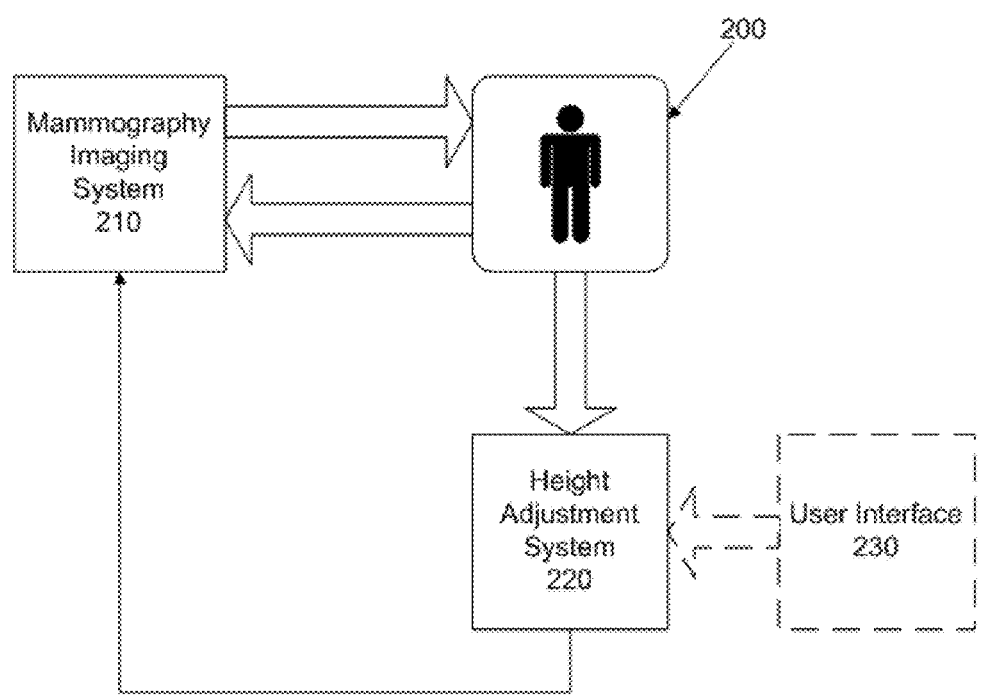
FIG. 2 is a block diagram of a mammography imaging system with automated height adjustment system as described in an embodiment of the invention.

FIG. 2 is a block diagram of a mammography imaging system with an automated height adjustment system as described in an embodiment of the invention. The mammography system 210 is provided with a height adjustment system 220 configured to automatically position the mammography system for imaging based on a patient's 200 breast height level. The mammography system 210 is configured to acquire the patient images. The height adjustment system 220 is connected to the mammography system 210 and is configured to control the movement of the mammography system 210 as a whole, or parts of the system, to align it for patient imaging. The height adjustment system 220 positions the mammography system 210 based on the patient breast height level. In an embodiment, the patient breast height level is recorded during the initial mammography procedure and the recorded information is used in positioning the mammography system 210 during the subsequent mammography procedures. Optionally, a user interface 230 may be provided to provide the breast height level information of a patient such that the height adjustment system 220 can position the mammography system automatically. The user interface 230 could be used, during an initial mammography procedure or if the recorded patient breast height level information is not available.

Figure 3:
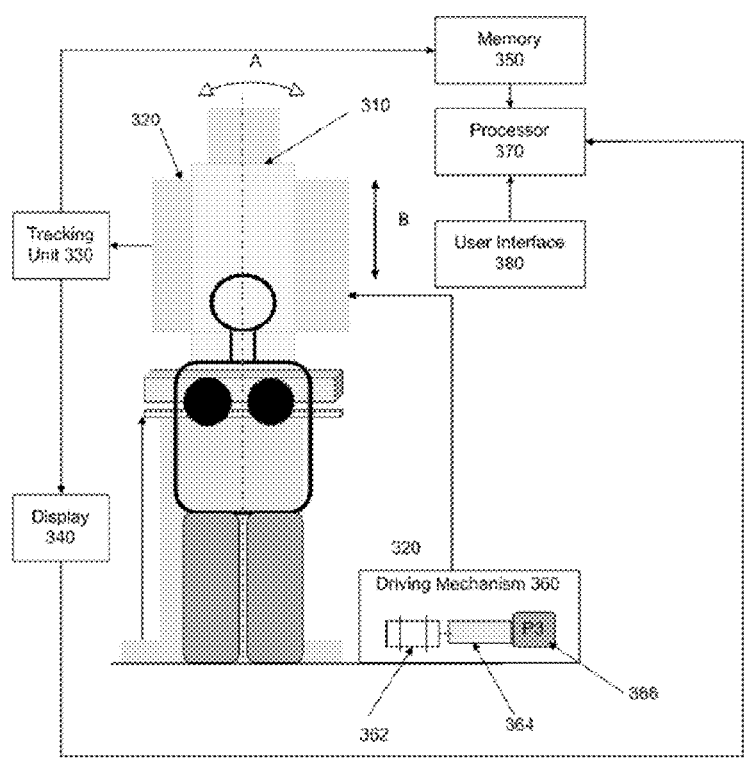
FIG. 3 is a diagrammatic representation of a mammography imaging system with automated height adjustment system as described in an embodiment of the invention.

FIG. 3 is a diagrammatic representation of a mammography imaging system capable of automatically adjusting the gantry position as described in an embodiment of the invention. The mammography system includes a vertical member 310 and a gantry 320 attached to the vertical member 310. The gantry 320 is movable along the vertical member 310. Gantry 320 movements are shown by arrow lines A and B. The gantry 320 includes an X-ray source, image receptor, compression plate and related accessories. While performing the imaging, the breast is placed on the compression plate and gantry 320 needs to be positioned to accommodate the breast. Before imaging, the gantry position is adjusted corresponding to patient's breast height level. The imaging system further includes a tracking unit 330 to track the gantry position. The gantry position could be tracked using a potentiometer or a measuring scale provided on the vertical member. Patient's breast height is measured from a fixed reference. The tracking unit 330 is connected to the gantry 320 such that it tracks the position of the gantry. The imaging system could include a display 340 wherein the tracked gantry position or the corresponding patient's breast height may be displayed.

The imaging system further comprises memory 350 configured to store the tracked gantry position or corresponding breast height level. The tracking unit 330 may provide patient breast height level or the gantry position to the memory 350 and may store the information in the memory 350. The memory 350 could be the internal memory of the imaging system or an external database. For purposes of simplicity, devices that can read and/or write media on which computer programs are recorded are also included within the scope of the term "memory." A non-exhaustive list of media that can be read with such a suitable device includes CDs, CD-RWs, DVDs of all types, magnetic media (including floppy disks, tape, and hard drives), flash memory in the form of sticks, cards, and other forms, ROMs, etc. . . . , and combinations thereof. The memory may also include random access memory (RAM), read-only memory (ROM), electrically programmable memory (EPROM), etc. . . .

A drive mechanism 360 is provided to adjust the gantry position in accordance with the patient's breast height level. The drive mechanism 360 could include a motor unit 362 and a control unit 364 configured to control the motor 362. The drive mechanism 360 could also include plurality of user controls 366 to control the drive mechanism 360 thereby controlling the movement of the gantry 320. The user controls 366 could be hand or pedal operated based on the convenience of the user.

The system further includes a processor 370 configured to control the imaging operation. The processor 370 processes the image data acquired. In an embodiment, the processor 370 is configured to control the drive mechanism 360. In an embodiment, the processor 370 is configured to receive the patient information and, based on the patient information, accesses the gantry position or breast height level corresponding to the patient from the memory 350. Alternately, the processor 370 may receive the gantry position or breast height level information through a user interface 380 and may control the drive mechanism 360 accordingly.

Figure 4:
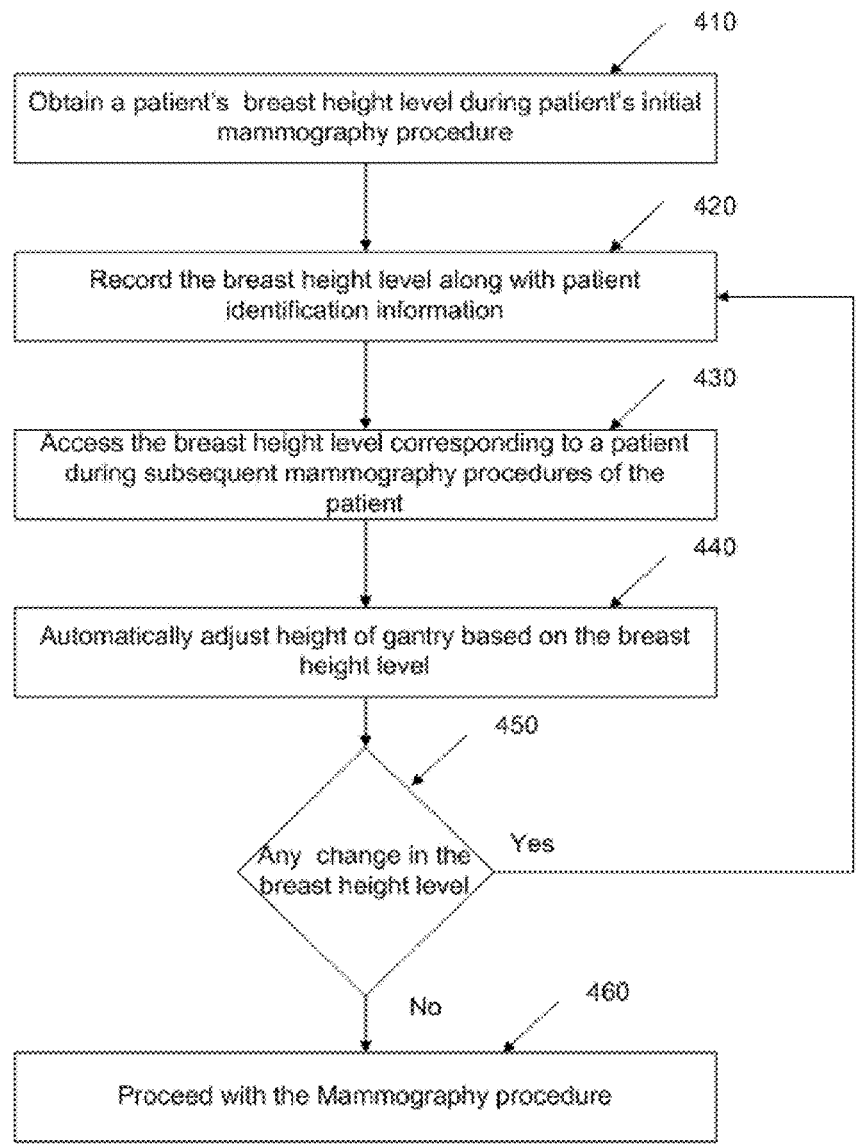
FIG. 4 is a flowchart illustrating a method of automatically adjusting the gantry position in a mammography procedure as described in an embodiment of the invention.

FIG. 4 is a flowchart illustrating a method of automatically adjusting the gantry position in a mammography procedure as described in an embodiment of the invention. At step 410, the patient's breast height level is obtained during the patient's initial mammography procedure. The patient's breast level could be obtained from the patient and through a user interface. Patient's breast height level could be measured initially and the gantry position may be adjusted accordingly. At step 420, the patient breast height level is recorded along with patient identification information. This could be recorded along with the patient information in the internal memory or external database. This will be part of the patient information and a clinician will be able to access this information later. Instead of patient breast height level, the corresponding gantry position such as gantry height from a fixed reference could be noted and stored in the memory. At step 430, the patient's breast height level is accessed, during the subsequent mammography procedures. If the recorded breast height level or the gantry position is available from the earlier mammography procedures or by any other means, that information is accessed. At step 440, using the accessed breast height level information, the gantry position is adjusted. The gantry position could be adjusted automatically upon detecting the patient for a mammography procedure. During initial mammography procedure, the breast height level could be obtained from the patient or through a user interface and the gantry may be positioned automatically. At step 450, a check could be made to confirm whether there is any change in the patient breast height level or the gantry position from the recorded level. If there is a change, the updated height level is recorded as at step 420, otherwise the mammography imaging procedure is performed as at step 460.

Figure 5:
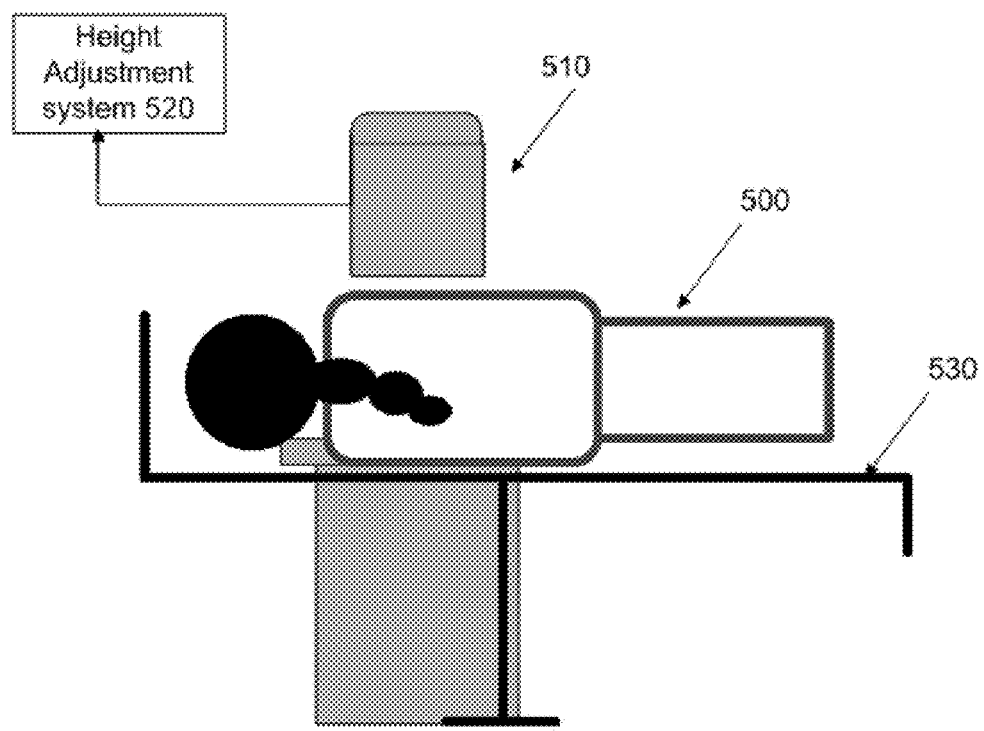
FIG. 5 is a diagrammatic representation of a mammography imaging system with automated height adjustment system as described in another embodiment of the invention.

FIG. 5 is a diagrammatic representation of a mammography imaging system with an automated height adjustment system as described in an embodiment of the invention. The gantry position is adjusted while the patient is in a recumbent position. The patient 500 is lying on patient table 510. The patient breast height level is obtained by a patient adjustment system 520, using at least one of the methods described above, and the gantry 530 is adjusted based on the patient breast height level. In an embodiment, along with beast height level or gantry position information, the patient table position could be recorded. Alternately, the patient table position including the table height is recorded during the initial mammography procedure and is used in automatically adjusting the breast height level by adjusting the patient table, during the subsequent mammography procedures.

Although embodiments of the invention are explained with reference to recording gantry position, patient breast height level, and the patient table position, the invention is applied to recording any parameter that will help the clinician in positioning the gantry. Any other parameter, such as different physical parameters of the patient, could be recorded during the initial mammography procedure and that information could be accessed during subsequent procedures to assist the technician in positioning the gantry.

The advantages of various embodiments of the invention include, but are not limited to: automatic real time positioning of the mammography X-ray system to the desired breast level based on previously recorded patient's breast height level. The processor is configured to retrieve patient's breast height information from patient history records and communicate the same to the drive mechanism for auto positioning the gantry to breast level. The invention further provides a method for auto initiation of the drive mechanism upon detection of patient information. Dynamic updating of patient's breast height information in the patient history record, along with patient identification information during subsequent hospital visits in case any change in height, is observed. The height adjustment system described is highly precise and simple to use. The system improves the efficiency of the system and reduces the wait time of the patient.

The above-description of the embodiments of the methods and systems has the technical effect of automatically positioning the gantry based on the previously recorded patient breast level.

Thus various embodiments of the invention describe a method and system for automatically determining the laterality of breasts in a mammography imaging procedure.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments are described above in detail. The assemblies and methods are not limited to the specific embodiments described herein, but rather, components of each assembly and/or method may be utilized independently and separately from other components described herein. Further the steps involved in the workflow need not follow the sequence in which there are illustrated in figures and all the steps in the work flow need not be performed necessarily to complete the method.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We Claim:

1. An automated height adjustment system for a mammography imaging system having a movable gantry associated with a fixed vertical support, the automated height adjustment system comprising:
    a tracking unit for tracking a patient's breast height level during the patient's initial mammography procedure;
    memory for storing the tracked breast height level along with patient identification information;
    a processor configured to access the breast height level using the patient identification information during subsequent mammography procedures for the patient; and
    a drive mechanism capable of automatically adjusting the height of the gantry based on the accessed breast height level;
    wherein the processor is further configured to automatically determine the presence of the patient and, upon detecting the patient, to access the breast height level and automatically adjust the height of the gantry in response thereto.

2. The system as claimed in claim 1, wherein the breast height level of the patient is a lowest breast height level from a fixed reference.

3. The system as claimed in claim 1, further comprising:
    a display for displaying the breast height level of the patient.

4. The system as claimed in claim 1, further comprising:
    a user interface associated with the processor for providing the patient's breast height level.

5. The system as claimed in claim 1, wherein the tracking unit is configured to track updated breast height level during each mammography procedure and communicates the breast height level to the memory.

6. The system as claimed in claim 1, wherein the tracking unit is configured to track gantry height during each mammography procedure and communicate to the memory.

7. The system as claimed in claim 1, wherein the memory is configured to store the patient breast height level during subsequent mammography procedures, if the patient height is different from the initial recorded patient breast height level.

8. The system as claimed in claim 1, wherein the processor is further configured to automatically determine the presence of the patient from an identification device provided on the patient.

9. A mammography system, comprising:
    a fixed vertical member;
    a movable gantry, movable along the vertical member having an X-ray source and an image receptor;
    a tracking unit configured to track gantry position corresponding to a breast height level in a mammography procedure;
    memory configured to record the tracked gantry position corresponding to the breast height level;
    a drive mechanism configured to adjust the gantry position; and
    a processor coupled with the drive mechanism;
    wherein the processor is configured to access the tracked gantry position and instruct the drive mechanism to adjust the gantry position based on the tracked gantry position; and
    wherein the processor is further configured to automatically determine the presence of a patient and, upon detecting the patient, to access the recorded tracked gantry position corresponding to the patient's breast height level and automatically adjust the height of the gantry in response thereto.

10. The mammography system as claimed in claim 9, wherein the processor is further configured to automatically determine the presence of the patient from an identification device provided on the patient.

11. A method of automatically adjusting gantry position during a mammography procedure, the method comprising:
    obtaining a patient's breast height level during an initial mammography procedure;
    recording in a computer memory the patient's breast height level along with patient identification information;
    during subsequent mammography procedures for the patient, automatically determining the presence of the patient to access the patient's breast height level and automatically adjusting the height of the gantry based on the patient's breast height level.

12. The method as claimed in claim 11, wherein the step of obtaining a patient's breast height level during an initial mammography procedure comprises:
    obtaining the patient's breast height level at least from one of the patient and a user interface;
    adjusting the gantry position based on the patient's breast height level; and
    obtaining gantry position information corresponding to the patient's breast height level.

13. The method as claimed in claim 11, wherein the step of obtaining a patient's breast height level during an initial mammography procedure comprises:
    calculating the patient's breast height level from the patient's demographic and physiological information.

14. The method as claimed in claim 11, wherein the recording step comprises:
    recording the gantry position or the patient's breast height level in an electronic medical record (EMR) for each mammography procedure.

15. The method as claimed in claim 11, wherein the recording step comprises:
    recording the gantry position or the patient's breast height level in an internal memory of a mammography imaging system for the subsequent mammography procedures.

16. The method as claimed in claim 11, wherein the step of automatically determining the presence of the patient comprises automatically determining the presence of the patient from an identification device provided on the patient.

* * * * *